United States Patent
Zaiki et al.

(10) Patent No.: US 8,831,169 B2
(45) Date of Patent: Sep. 9, 2014

(54) X-RAY DIAGNOSIS APPARATUS AND A METHOD FOR CONTROLLING AN X-RAY IRRADIATION REGION

(75) Inventors: Ryuji Zaiki, Tochigi-ken (JP); Reiko Hashimoto, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 204 days.

(21) Appl. No.: 13/437,292

(22) Filed: Apr. 2, 2012

(65) Prior Publication Data

US 2012/0189093 A1 Jul. 26, 2012

Related U.S. Application Data

(63) Continuation of application No. 12/836,169, filed on Jul. 14, 2010, now Pat. No. 8,213,569.

(30) Foreign Application Priority Data

Jul. 14, 2009 (JP) ................ P2009-166071

(51) Int. Cl.
*A61B 6/00* (2006.01)
*A61B 6/08* (2006.01)
*A61B 6/06* (2006.01)
*G21K 1/04* (2006.01)
*A61B 6/03* (2006.01)

(52) U.S. Cl.
CPC . *A61B 6/035* (2013.01); *A61B 6/08* (2013.01); *A61B 6/06* (2013.01); *A61B 6/542* (2013.01); *A61B 6/469* (2013.01); *G21K 1/04* (2013.01); *A61B 6/4441* (2013.01)
USPC .......................................... 378/16; 378/150

(58) Field of Classification Search
CPC ............ A61B 6/032; A61B 6/06; A61B 6/54; A61B 6/542; A61B 6/488; A61B 6/467; A61B 6/469; G21K 1/02; G21K 1/04; G21K 1/046
USPC .................. 378/4, 16, 114, 145, 147–153
See application file for complete search history.

(56) References Cited

U.S. PATENT DOCUMENTS

| | | |
|---|---|---|
| 4,143,273 A | 3/1979 | Richey et al. |
| 4,200,800 A | 4/1980 | Swift |
| 4,450,578 A | 5/1984 | Hill |

(Continued)

FOREIGN PATENT DOCUMENTS

| | | |
|---|---|---|
| JP | 2000-217035 | 8/2000 |
| JP | 2004-180715 | 7/2004 |
| JP | 2009-82205 | 4/2009 |

*Primary Examiner* — Jurie Yun
(74) *Attorney, Agent, or Firm* — Oblon, Spivak, McClelland, Maier & Neustadt, L.L.P.

(57) ABSTRACT

An X-ray diagnosis apparatus and a method for controlling an X-ray irradiation region that can appropriately narrow down an X-ray radiation aperture so as to fit a configuration of a region of interest during acquisition of X-ray projection data for reconstructing tomography images of an object. Based on a plurality of 2D image data acquired through a preliminarily X-ray imaging, a 3D region of interest is set up on an examination target portion having a strong directionality. X-ray imaging of the 3D region of interest is performed by sliding and rotating a plurality of aperture blades in an X-ray collimator based on a projected figure of the 3D region of interest along successively renewed imaging directions around a periphery of an object.

9 Claims, 13 Drawing Sheets

(56) References Cited

U.S. PATENT DOCUMENTS

| | | |
|---|---|---|
| 4,998,268 A | 3/1991 | Winter |
| 5,818,902 A | 10/1998 | Yu |
| 6,023,494 A | 2/2000 | Senzig et al. |
| 6,266,393 B1 | 7/2001 | Ein-Gal |
| 6,449,335 B1 | 9/2002 | Siochi |
| 6,501,828 B1 | 12/2002 | Popescu |
| 6,600,810 B1 | 7/2003 | Hughes |
| 7,082,189 B2 | 7/2006 | Yahata et al. |
| 7,095,823 B2 | 8/2006 | Topolnjak et al. |
| 2003/0086530 A1 | 5/2003 | Otto |
| 2004/0202283 A1 | 10/2004 | Okumura et al. |
| 2006/0256915 A1 | 11/2006 | Otto et al. |
| 2007/0009080 A1 | 1/2007 | Mistretta |
| 2008/0247503 A1 | 10/2008 | Lauritsch et al. |

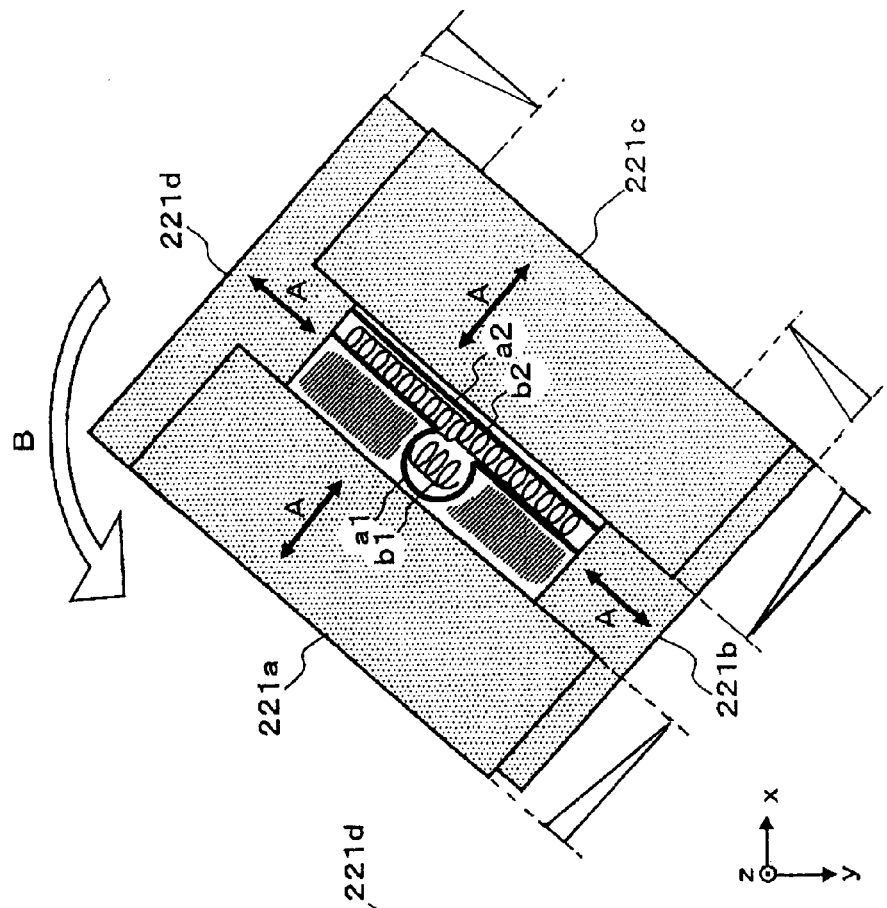
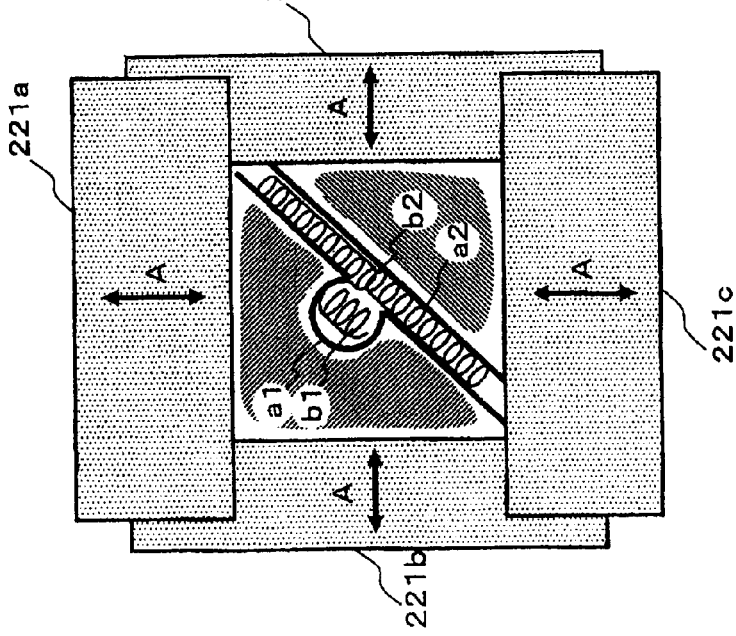

X-RAY DIAGNOSIS APPARATUS AND A METHOD FOR CONTROLLING AN X-RAY IRRADIATION REGION

CROSS-REFERENCE TO RELATED APPLICATIONS

This application is a continuation of U.S. application Ser. No. 12/836,169 filed Jul. 14, 2010, and is based on and claims the benefit of priority from Japanese Patent Application No. 2009-166071, filed on Jul. 14, 2009, the entire contents of each of which are expressly incorporated herein by reference.

BACKGROUND

A. Field

Embodiments described herein relate generally to an X-ray diagnosis apparatus and a method for controlling an X-ray irradiation region, and more particularly, to an X-ray diagnosis apparatus and a method for controlling an X-ray irradiation region that can appropriately narrow down an X-ray radiation aperture so as to fit a configuration of a region of interest during acquisition of X-ray projection data for reconstructing tomography images of an object.

B. Background

Recent years, medical image diagnosis by using an X-ray diagnosis apparatus, an X-ray computer tomography (CT) apparatus or a magnetic resonance instrument (MRI) apparatus, has widely applied for cardiovascular diagnosis and following observation of cardiology in accompany with a development of catheter techniques.

Usually, for performing angiography, two dimensional (2D) or three dimensional (3D) image data is generated by reconstructing X-ray image data acquired through X-ray irradiations over the diagnosis target region along directions more than 180 degrees around the target region. In this case, when some region would have been dropped out from the acquired image, the reconstructed image appears artifacts. To avoid this, for acquiring 2D or 3D images, X-ray irradiations have performed in a wide viewing field so as to sufficiently cover the imaging portion in 180 degrees. As a result, a serious problem of exposure dose on an object has been increased since X-rays are irradiated on unnecessary portion other than a region of interest in a diagnosis target region.

Generally, an X-ray diagnosis apparatus includes an X-ray generator and an X-ray detector so as to face each other by holding them on a C-arm holder. Further, a collimator is provided between the X-ray generator and the X-ray detector. The collimator includes a plurality of aperture blades for setting up a size and a position of an aperture so as that X-rays emitted from the X-ray generator selectively irradiates onto an examination target portion of an object.

A conventional method has been proposed to reduce X-ray exposure dose to an object by moving the aperture blades in an approaching or a seceding direction to or from a center axis of X-ray beams so as to irradiate X-rays onto the diagnosis target region.

The aperture blades in the conventional collimator can be moved merely in an approaching or a seceding directions to or from a center axis of X-ray beams. Accordingly, when a diagnosis target region has a spherical shape, such as a skull bone, having almost equal expanses in every direction, unnecessary X-ray irradiations can be effectively eliminated. However, as illustrated in FIG. 5A, when X-ray irradiations are performed to a diagnosis target region having a strong directionality, such as blood vessels, in the cardiovascular diagnosis, X-rays irradiated onto unnecessary regions of the diagnosis. This causes a serious problem of unnecessary X-ray exposure doses.

BRIEF DESCRIPTION OF THE DRAWINGS

The accompanying drawings, which are incorporated in and constitute part of this specification, illustrate various embodiments and/or features of the present invention, and together with the description, serve to explain embodiments of the present invention. Where possible, the same reference number will be used throughout the drawings to describe the same or like parts. In the drawings:

FIGS. 5A and 5B illustrate X-ray imaging operations of an examination target portion by limiting an irradiation region through the movable collimator depicted in FIG. 4.

DETAILED DESCRIPTION

Figure 1:
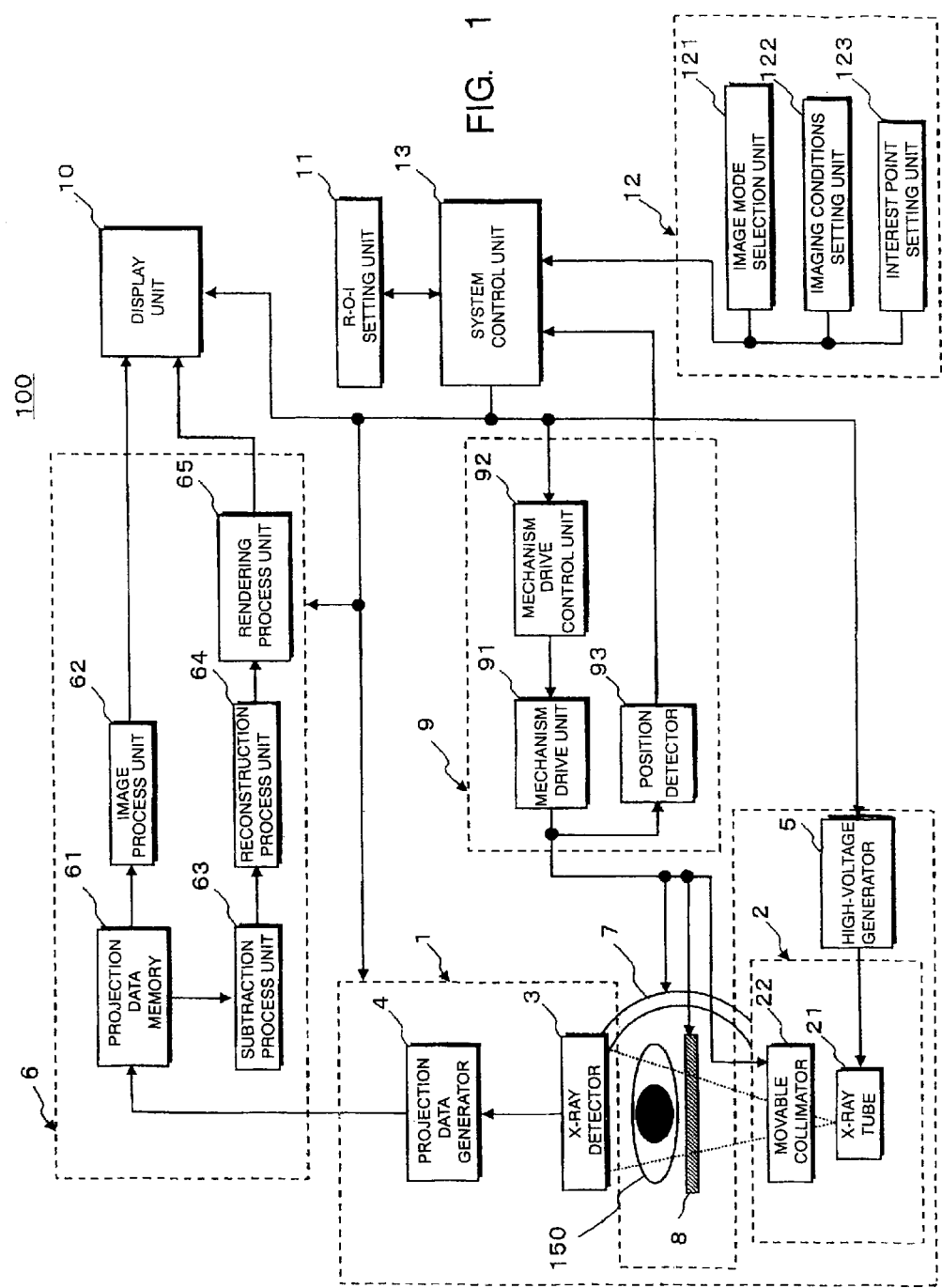
FIG. 1 is a block diagram illustrating a total construction of an X-ray diagnosis apparatus consistent with an embodiment of the present invention.

The exemplary embodiments consistent with the present invention addresses these and other problems and drawbacks and provides an X-ray diagnosis apparatus and a method for controlling X-ray exposure dose that can eliminate unnecessary X-ray irradiations onto periphery of a target region and can reduce X-ray exposure dose to the object by sliding and/or turning a plurality of aperture blades in an X-ray collimator based on a figure of the target region having a strong directionality.

According to certain exemplary embodiments, an X-ray diagnosis apparatus object includes an X-ray tube configured to generate X-rays to an examination target portion of an object, an X-ray detecting unit configured to detect X-rays penetrated through the object, an X-ray collimating unit including a plurality of aperture blades for setting an irradiation region of the X-rays generated from the X-ray tube and a driving unit configured to rotationally move the X-ray tube and the X-ray detecting unit. The X-ray diagnosis apparatus object further includes an image data generating unit configured to generate image data by performing a reconstruction process based on projection data detected in accompany with the rotationally movements along a plurality of different imaging directions by the X-ray detecting unit, a region of interest setting unit configured to set up a region of interest on the examination target portion, and an X-ray aperture controlling unit configured to control the X-ray collimating unit so as to slide and turn the aperture blades in accompany with the rotationally movements, based on the set up data of the region of interest and the imaging direction.

According to another exemplary embodiment, a method is provided for controlling X-ray exposure dose includes generating X-rays from an X-ray tube to an examination target region of an object; detecting X-rays penetrated through the object by an X-ray detecting unit; setting up an X-ray irradiation region a plurality of aperture blades through an X-ray collimating unit; and rotationally moving the X-ray tube and the X-ray detecting unit. The controlling method further includes generating image data by performing a reconstruction process of a plurality of different imaging directions based on projection data of a plurality of different imaging directions detected by the X-ray detecting unit in accordance with the rotationally movements; setting up a region of interest to the examination target region; and controlling the X-ray collimating unit so as to slide and move the aperture blades in accordance with the rotationally movement based on the set up data of the region of interest and the imaging directions.

According to one exemplary embodiment, when image data is generated based on projection data acquired through X-ray irradiations to a region of interest of an object, unnecessary X-ray irradiations to the periphery of the region of interest can be inhibited by sliding and/or turning aperture blades of a movable collimator based on a figure of the region of interest having a strong directionality in a prescribed direction. Consequently, X-ray exposure dose in the X-ray imaging to the object can be reduced.

In the following exemplary embodiment consistent with the present invention, X-ray diagnosis apparatus initially sets up a 3D region of interest on an examination target portion (blood vessel site) having a strong directionality, based on a plurality of 2D image data acquired through X-ray imaging in a preliminary imaging mode to an object. The imaging direction is successively renewed by turning the imaging system at a periphery of the object. Then, X-ray imaging in an actual imaging mode is performed to the examination target portion before and after administrating a contrast agent by sliding and/or turning the aperture blades in the movable collimator based on a projected figure of the 3D region of interest to each of the imaging directions. A volume data is generated by performing a reconstruction process of a difference projection data generated through a subtraction process between a mask projection data acquired through the X-ray imaging before administrating the contrast agent and a contrast projection data acquired through the X-ray imaging after administrating the contrast agent. 3D image data of the examination target portion is generated by performing a rendering process of the volume data.

FIG. 1 is a block diagram illustrating a construction of the X-ray diagnosis apparatus. The X-ray diagnosis apparatus 100 includes an X-ray imaging unit, an X-ray generating unit 2, an X-ray detecting unit 3, an image data generating unit 6, a holding unit 7, a bed unit 8 and a moving mechanism drive unit 9.

Both in a preliminary imaging mode for setting a region of interest of an examination target site (blood vessel site) in an object 150 on devices placed in a blood vessel, such as a stent or coils, and in an actual imaging mode for observing the placed blood vessel devices in the examination target site, the X-ray imaging unit 1 generates projection data by irradiating X-rays on the examination target portion and by detecting the X-rays penetrated through the target portion. The image data generating unit 6 generates 2D image data of a wide range based on the projection data acquired in the preliminary imaging mode. The image data generating unit 6 further generates 3D image data of a narrow range based on the projection data acquired in the actual imaging mode. The holding unit 7 supports the X-ray generating unit 2 and the X-ray detecting unit 3 for moving in prescribed directions around a periphery of an object 150. Hereinafter these units are collectively referred to as an "imaging system". The bed unit 8 moves a top plate placing an object 150 in a prescribed direction. The moving mechanism drive unit 9 supplies drive signals to various moving mechanisms provided in the holding unit 7 and the bed unit 8. The moving mechanism drive unit 9 further detects position data of the imaging system and the top plate based on these drive signals.

The X-ray diagnosis apparatus 100 further includes a display unit 10, a region of interest setting unit 11, an input unit 12 and a system control unit 13. The display unit 10 displays 2D image data in a preliminary imaging mode and a 3D image data in an actual imaging mode generated through the image data generating unit 6. Based on an interest point indicated by the input unit 12, the region of interest setting unit 11 sets up a 3D region of interest to the examination target portion indicated in the 2D image data. The input unit 12 inputs object data and various command signals, and sets up X-ray imaging conditions including an X-ray irradiation condition, imaging directions in a preliminary imaging mode and an actual imaging mode and image data generating conditions, and designates interest points on 2D image data in the preliminary imaging mode. The system control unit 13 totally controls each of the units.

The X-ray imaging unit 1 includes, as illustrated in FIG. 1, an X-ray generating unit 2, an X-ray detecting unit 3, a projection data generating unit 4 and a high voltage generating unit 5. The X-ray imaging unit 1 generates projection data based on X-rays penetrated through an object 150 by performing X-ray irradiation s both in a preliminary imaging mode and in an actual imaging mode. In the preliminary imaging mode, X-ray irradiation is performed in a wide range by sliding and turning aperture blades of a movable collimator provided in the X-ray generating unit 2. In the actual imaging mode, X-ray irradiation is performed in a narrow range by sliding and turning the aperture blades of the movable collimator.

Figure 2:
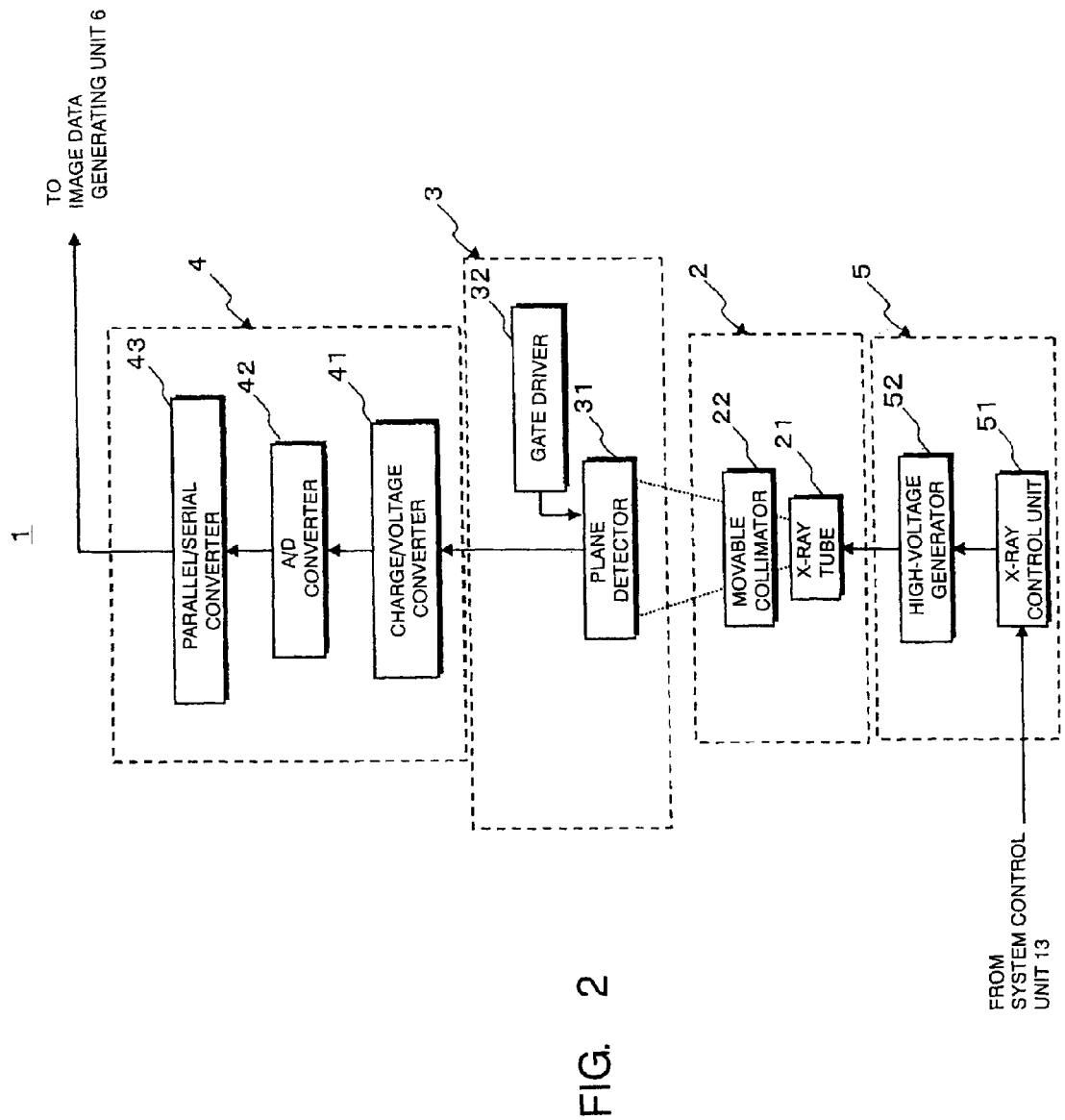
FIG. 2 is a block diagram illustrating a construction of the X-ray imaging unit provided in the X-ray diagnosis apparatus shown in FIG. 1.

FIG. 2 illustrates a construction in the X-ray imaging unit 1, the X-ray generating unit 2 and the high voltage generating unit 5. The X-ray generating unit 2 includes an X-ray tube 21 for irradiating X-rays onto an examination target region and a movable collimator 22 for forming X-ray cone beams irradiated from the X-ray tube 21. The X-ray tube 21 generates X-rays by accelerating electrons emitted from a filament in a high voltage and by bombarding to a tungsten anode plate. The movable collimator 22 is used both for reducing an exposure dose over an object 150 and for increasing a quality of image data.

Figure 3:
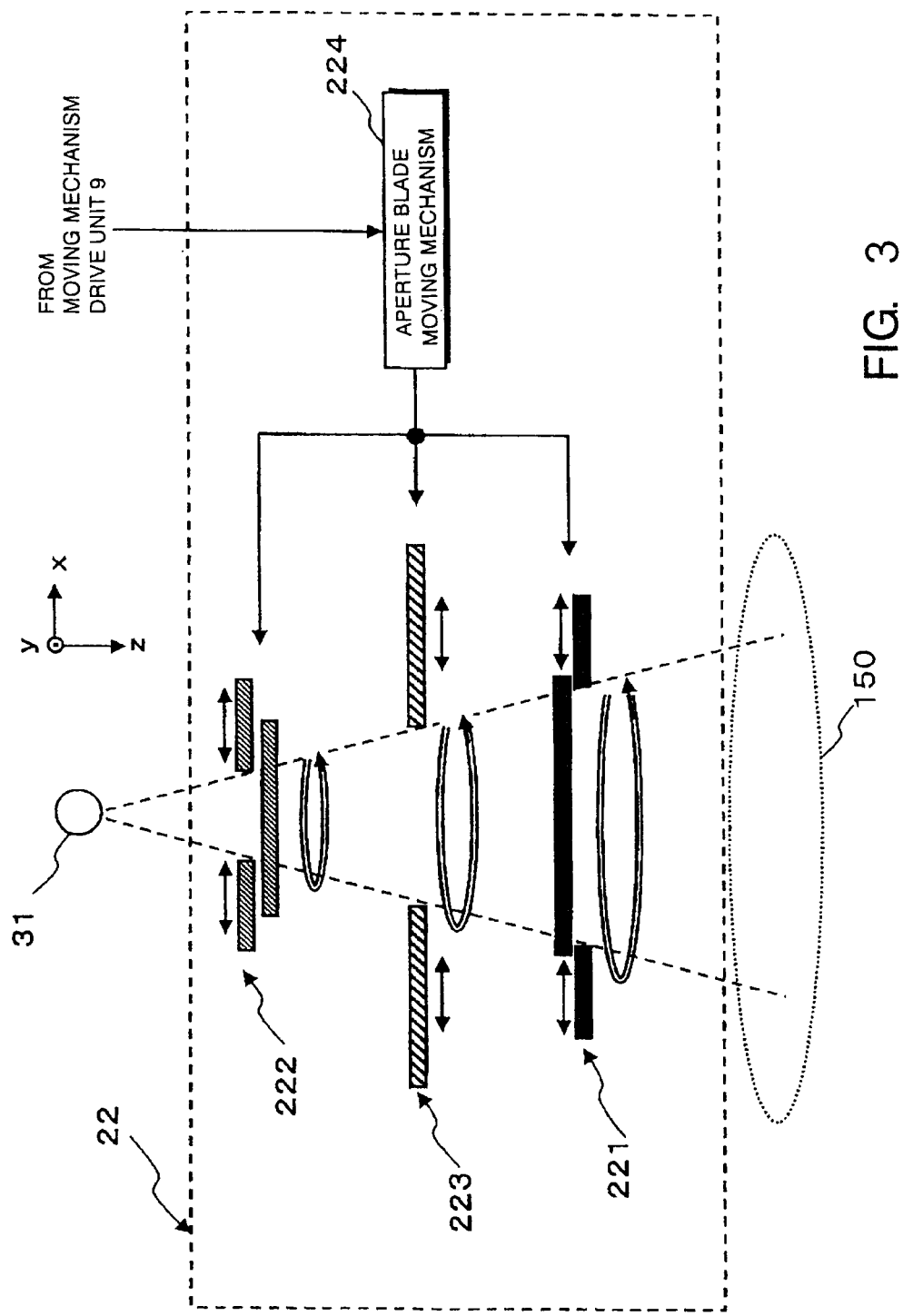
FIG. 3 depicts a construction of the movable collimator provided in the X-ray imaging unit shown in FIG. 2.

FIG. 3 illustrates a construction of the movable collimator 22. The movable collimator 22 includes a plurality aperture blades (upper blades) 221, a plurality of lower blades 222 and a plurality of compensation filters 223. The plurality of upper blades 221 narrows the X-rays emitted from the X-ray tube 21 down to an irradiation region in a preliminary imaging mode and in an actual imaging mode. The plurality of lower blades 222 reduces scattered rays and leakage dose by moving in connection with the upper blades 221. The compensation filter 223 prevents halation by selectively reducing X-rays penetrated through penetrated through media having a low dosage. The movable collimator 22 further includes an aperture blade moving mechanism 224. The aperture blade moving mechanism 224 moves and turns the plurality of aperture blades 221, the plurality of lower blades 222 and the plurality of compensation filter 223 in prescribed positions through wire ropes and pulleys.

Figure 4:
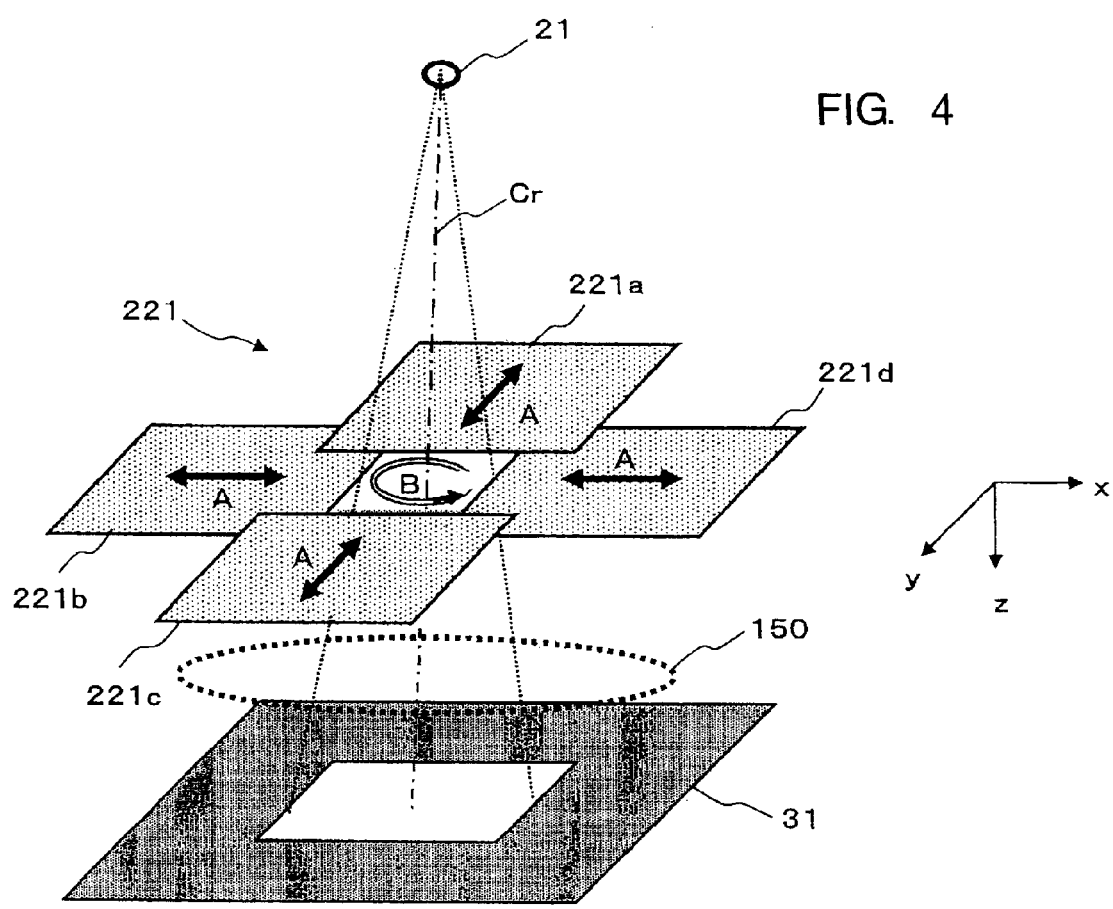
FIG. 4 depicts a construction of the aperture blades provided in the movable collimator shown in FIG. 3.

FIG. 4 depicts a construction and function of the plurality of aperture blades (upper blades) 221 provided in the movable collimator 22. To avoid redundant explanations, the construction and function of the plurality of lower blades 222 and the compensation filters 223 that are moved in conjunction with the plurality of upper blades 221 are omitted.

As illustrated in FIG. 4, the X-ray tube 21 and the plane detector 31 of the X-ray detecting unit 3 are provided so as to face the object 150 each other. A plurality of aperture blades (upper blades) 221 of the movable collimator 22 is provided between the X-ray tube 21 and the object 150. The upper blades 221 is constructed by a set of four aperture blades 221a through 221d that can move in an approaching or a seceding direction (A direction) to or from a center axis Cr of X-ray beams and can rotate around a periphery of the center axis Cr in a prescribed direction (B direction). Each of the four aperture blades 221a through 221d is coupled to the pulley (not shown) of the aperture blade moving mechanism 224 (FIG. 3) through wire ropes (not shown).

Thus, the aperture blade moving mechanism 224 shown in FIG. 3 can voluntarily set up a size, a position and a direction of an X-ray irradiation region to an object 150 by moving each of the aperture blades 221a through 221d in the A direction and also by turning them in the B direction.

FIG. 5A illustrates an X-ray irradiation region set up by the conventional movable collimator. FIG. 5B illustrates an X-ray irradiation region set up by the movable collimator 22 having a rotating function of the aperture blades 221 consistent with the present invention. In these examples show X-ray irradiation regions for performing an X-ray imaging to follow by observation of an examination target site (a blood vessel site) in which a coil b1 is put in an aneurysm a1 and a stent b2 is put in a peripheral normal blood vessel a2. Such an examination target site has a strong directionality in a particular direction. Since the aperture blades in the conventional movable collimator can be moved merely in an approaching or a seceding to and from the center axis Cr of X-ray beams (FIG. 4), X-ray irradiation is performed on a relatively wider region including unnecessary regions for the examination as shown in FIG. 5A.

On the contrary, the movable collimator 22 consistent with the embodiment of the present invention can move the aperture blades 221a-221d so as to approach and secede to and from the center axis Cr of X-ray beams, and also can turn the aperture blades 221a-221d around the center axis. Consequently, as illustrated in FIG. 5B, despite a directionality of the examination target portion, unnecessary X-ray irradiations onto non-examination region can be significantly reduced. As a result, effective X-ray irradiations can be performed merely on the examination target region. Accordingly, it becomes possible to reduce exposure dose during an X-ray imaging in an actual imaging mode.

When a size of viewing filed of the X-ray irradiations is varied to reduce X-ray exposure dose to an object 150 by rotating the movable collimator 22, since an X-ray shielding characteristic of the aperture blade is uniformly fixed, significant intensity differences of contrast density would be occurred between a center portion and peripheral portions of projection image data. When image data is generated by reconstructing such projection image data having significant intensity differences of contrast density, the quality of the generated image data is deteriorated by the artifact generated due to non-continuity of the projection image data.

Figure 6A:
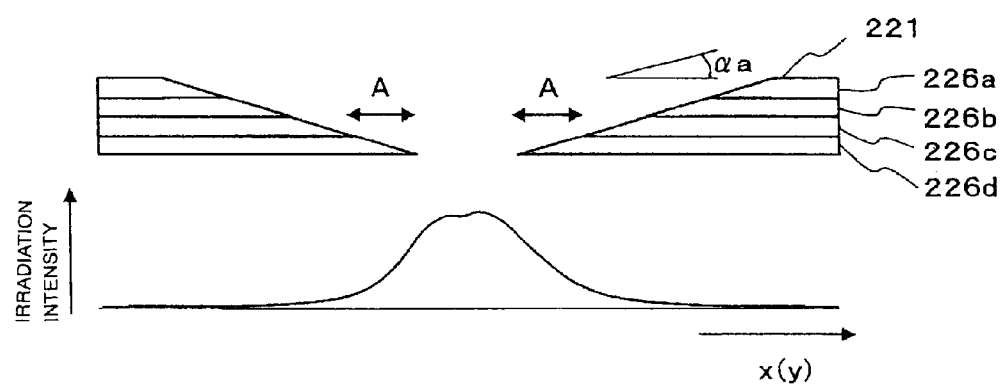
FIGS. 6A and 6B illustrate figured of the aperture blades used for the movable collimator shown in FIG. 4.
Figure 6B:
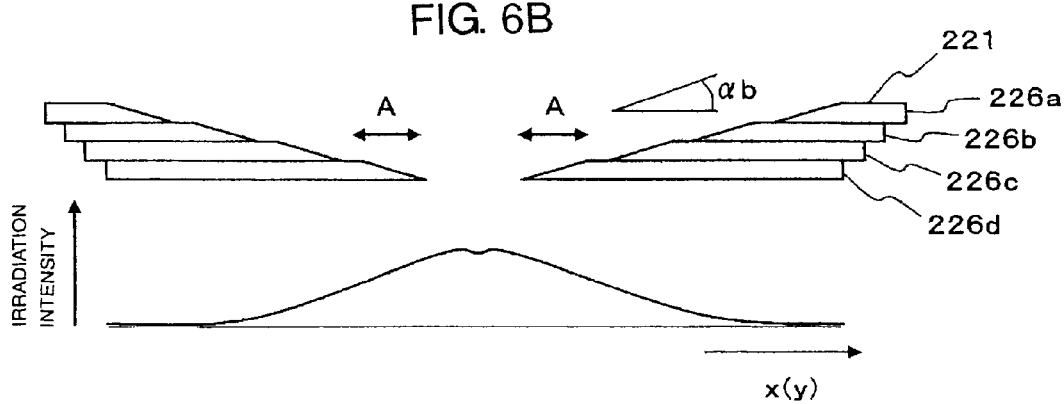

To avoid this problem, according to the embodiment consistent with the present invention, as illustrated in FIGS. 6A and 6B, the aperture blade can vary the X-ray shielding characteristics. For instance, as illustrated in FIG. 6A, each of four aperture blades 221a-221d is constructed by piling up a plurality N (e.g., N=4) of X-ray shielding plates 226a-226d that can slide in the A direction. Each of the X-ray shielding plates 226a-226d is connected to a pulley of the aperture blade moving mechanism 224 through a wire rope. The aperture blade moving mechanism 224 can arbitrarily set up an intensity distribution of projection data at periphery regions of the examination target region.

For instance, depending on the degree the non-continuity of the intensity distribution in the projection data, a moving amount of the respective X-ray shielding plates 226a-226d in the A direction is controlled. FIG. 6A depicts a configuration of the aperture blades 221 having an edge angle αa formed by the aperture blade moving mechanism 224 when the variation of the projection data at peripheral regions of the examination target region is relatively small. FIG. 6B illustrates a configuration of the aperture blades 221 having an edge angle αb (αb<αa) formed by the aperture blade moving mechanism 224 when the projection data largely varies at peripheral regions of the examination target region. The edge angle is automatically set up in accordance with a size of the examination target region or a size of 3D region of interest set up in the examination target region.

Turning back to FIG. 2, there are two kinds of methods for the X-ray detector 3 to detect cone beams irradiated from the X-ray generator 2. One is a method for using a plane detector and the other is a method for using an image intensifier (I.I.) or an X-ray television. As the X-ray detecting unit 3 in this embodiment, a plane detector is used for directly converting X-rays into charges. Of course, another type of the plane detector also can be used.

The plane detector 31 in the X-ray detecting unit 3 is constructed by two dimensionally arranging small detection elements in a column direction and a line direction. Each detection element includes a photoelectric film for generating charges depending on the irradiated X-rays, a condenser for accumulating the charges and a thin film transistor (TFT). To easy understanding, the plane detector 31 includes two detection elements arranged in a column direction (up and down direction of drawing) and a line direction (right and left direction of drawing).

Figure 7:
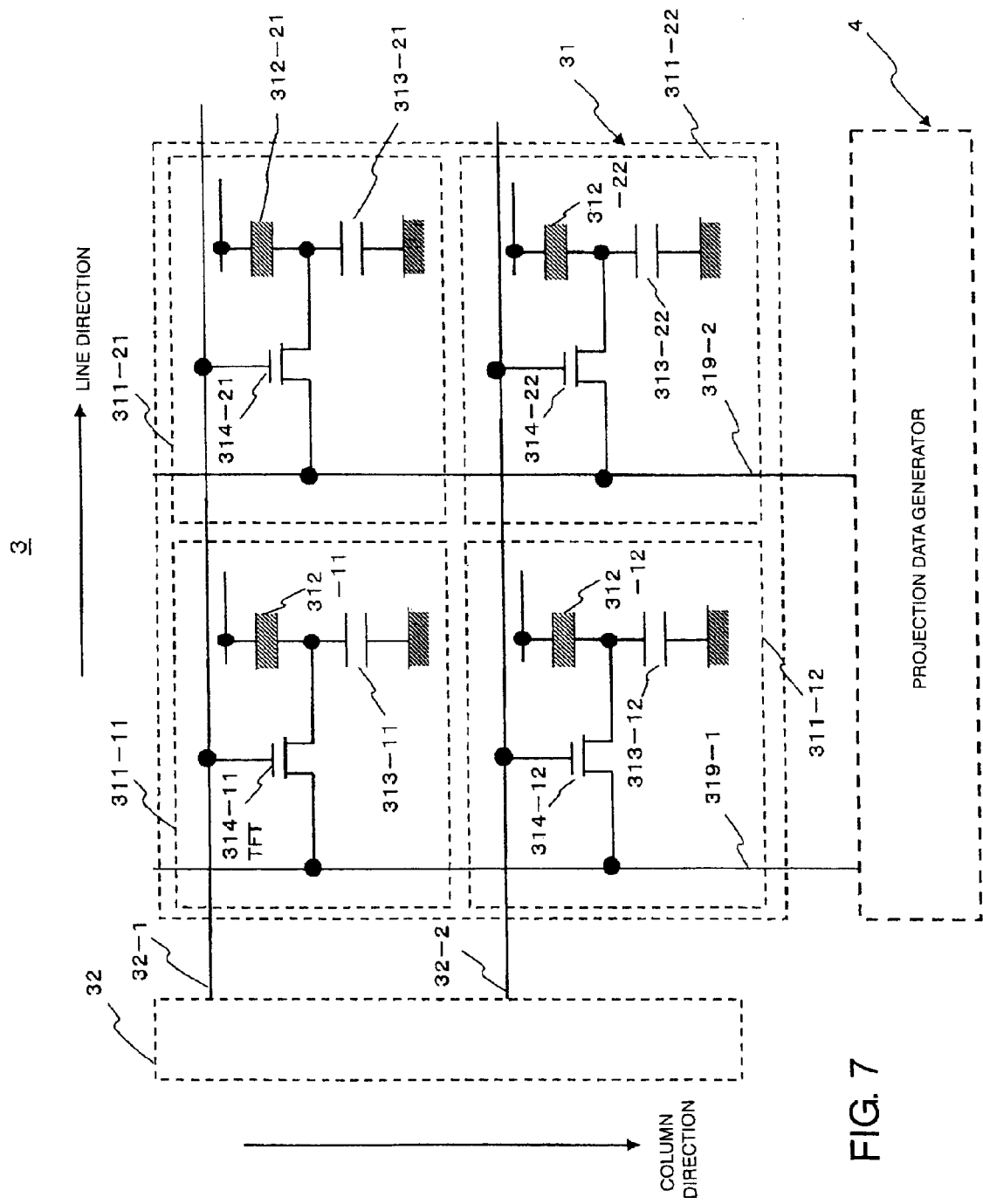
FIG. 7 shows a construction of the plane detector provided in the X-ray detecting unit depicted in FIG. 2.

As illustrated in FIG. 7, in the plane detector 31, a first terminal of the photoelectric films 312-11, 312-12, 312-21 and 312-22 is connected to a first terminal of the capacitors 313-11, 313-12, 313-21 and 313-22. Further, each connecting point is connected to a source terminal of the TFTs 314-11, 314-12, 314-21 and 314-22. Each of photoelectric films 312-11, 312-12, 312-21 and 312-22 is connected to a bias source (not shown), and a second terminal of the capacitors 313-11, 313-12, 313-21 and 313-22 is grounded. Further, each gate of the TFTs 314-11 and 314-21 along the line direction is commonly connected to an output terminal 32-1 of the gate driver 32, and each gate of the TFT 314-12 and TFT 314-22 is commonly connected to an output terminal 32-2 of the gate driver 32.

In the column direction, drain terminals of TFT 314-11 and 314-12 are commonly connected to a signal output line 319-1 and drain terminals of TFT 314-21 and 314-22 are commonly connected to a signal output line 319-2. The signal output lines 319-1 and 319-2 are connected to the projection data generating unit 4. A gate driver 32 supplies driving pulses to the gate terminal of TFT 315 for reading out signal charges accumulated in the capacitor 313 by the X-ray irradiation Referring FIG. 2, the projection data generating unit 4 includes a charge/voltage converter 41, an A/D converter 42 and a parallel/serial converter 43. The charge/voltage converter 41 converts charges read out from the plane detector 31 to voltages. The charges are readout in a parallel by a line or a column. The A/D converter 42 converts outputs from the charge/voltage converter 41 to digital signals. The parallel/serial converter 43 converts the digitalized parallel signals to time serial signals (projection data).

The high voltage generating unit 5 includes an X-ray control unit 51 and a high voltage generator 52. The high voltage generator 52 generates a high voltage for supplying between an anode and a cathode to accelerate thermal electrons generate from the cathode of the X-ray tube 21. The X-ray control unit 51 controls X-ray irradiation conditions, such as a tube current and a tube voltage in the high voltage generator 52, an irradiation time, and an irradiation timing, in accordance with instruction signals supplied from the system control unit 13

Referring again FIG. 1, the image data generating unit 6 includes a projection data memory 61, an image processing unit 62, a subtraction process unit 63, a reconstruction processing unit 64 and a rendering process unit 65. The projection data memory 61 generates two dimensional (2D) projection data by successively storing projection data supplied from the projection data generating unit 4 in the X-ray detecting unit 3 into a self memory circuit. For instance, in a preliminary imaging mode, two of 2D projection data are generated through X-ray irradiations along the orthogonally crossed imaging directions θa and θb set up to the object 150, and the 2D projection data are stored into the memory circuit in the projection data memory 61. In an actual imaging mode, before administrating a contrast agent into an object 150, a plurality M of 2D projection data (hereinafter referred to as "mask projection data") is generated through X-ray irradiations along the imaging direction θ1 through θM imaging direction θ1 through θM by continuously turning around the imaging system around a periphery of the object 150. And the mask projection data is stored with attaching the respective imaging directions as collateral data. Similarly, after administrating a contrast agent into the object 150, X-ray irradiation is performed to generate a plurality M of 2D projection data (hereinafter referred to as "contrast projection data") along the imaging direction θ1 through θM imaging direction θ1 through θM by continuously turning around the imaging system around the periphery of the object 150. And the contrast projection data is stored with attaching the respective imaging directions as collateral data. The imaging directions θ1 through θM in the actual imaging mode will be explained later in detail.

The image processing unit 62 includes an arithmetic circuit and a memory circuit (both are not shown). The arithmetic circuit reads out 2D projection data acquired along the imaging directions θa and θb in the preliminary imaging mode, and generates 2D image data (radiographic image data) for setting a region of interest by performing imaging processes, such as an interpolation process and a filtering process, to the 2D projection data. The acquired 2D image data is stored in the memory circuit.

The subtraction process unit 63 reads out mask projection data before administrating a contrast agent and projection data after administrating the contrast agent that region acquired along the imaging directions θ1 through θM in an actual imaging mode together their collateral imaging direction data from the memory circuit in the projection data memory 61. And the subtraction process unit 63 generates a plurality M of 2D difference projection data corresponded to the imaging directions θ1 through θM by applying the rotational digital subtraction angiography (DSA) method that performs a subtraction process between mask projection data and contrast projection data acquired along the same imaging direction. The acquired plurality M of difference projection data is stored in the memory circuit of the reconstruction processing unit 64 by adding data of imaging directions θ1 through θM.

The reconstruction processing unit 64 includes an arithmetic circuit and a memory circuit (both are not shown). The arithmetic circuit reads out the plurality M of difference projection data generated and stored in the subtraction process unit 63. And the reconstruction processing unit 64 generates 3D projection data by performing a reconstruction process of the difference projection data based on the collateral imaging direction data. Further, the reconstruction processing unit 64 generates volume data by processing a voxel interpolation of the 3D projection data. The rendering process unit 65 sets up opacity and a color tone based on the voxel value of the volume data generated by the reconstruction processing unit 64. The reconstruction processing unit 64 generates 3D image data (volume rendering image data) by performing a rendering process of the volume data based on the opacity and color tone, and an observing point and a line of sight supplied from the input unit 12.

Figure 8:
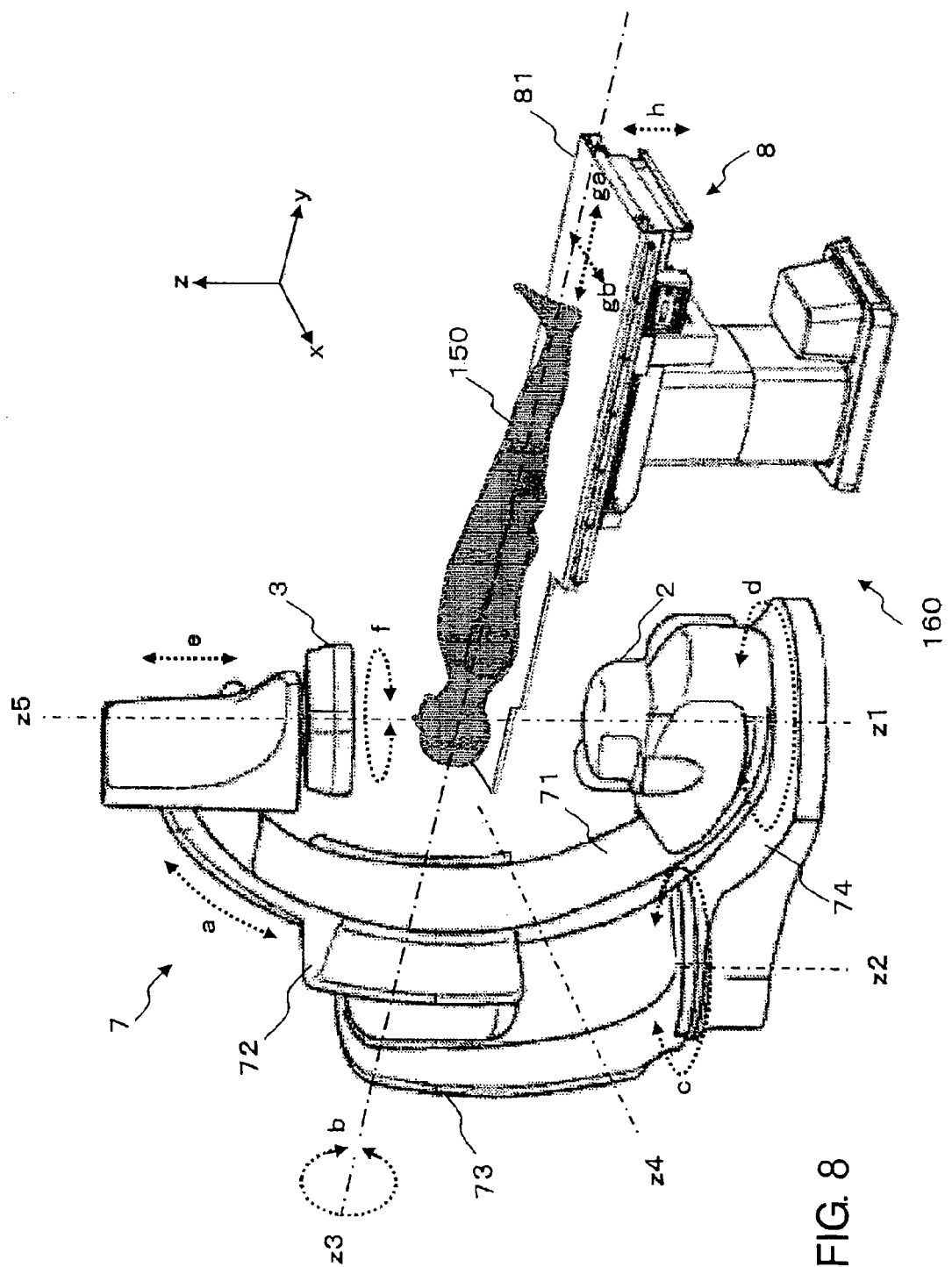
FIG. 8 depicts an embodiment of the holding unit and the bed unit provided in the X-ray diagnosis apparatus illustrated in FIG. 1.

FIG. 8 illustrates an practical construction of the holding unit 7 and the bed unit 8. The holding unit 7 has a C-arm 71 for supporting the X-ray generating unit 2 and the X-ray detecting unit 3 at each of the edges portions, respectively. The bed unit 8 has a top plate 81 for placing an object 150. To easily understand, a body axis direction of the object 150, e.g., a longitudinal direction of the top plate 81 is referred to as y-direction, a vertical direction to a floor surface 160 for providing the holding unit 7 and the bed unit 8 is referred to as z-direction, and an orthogonal direction to the y-direction and z-direction, e.g., a traversing direction of the top plate 81, is referred to as x-direction.

The holding unit 7 includes a C-arm 71, an arm holder 72, an arm brace member 73 and a floor circling arm 74. One edge portion of the floor circling arm 74 is rotatably mounted so as to rotate around a floor rotation axis z1 vertical to the floor surface 160 in the arrow direction d. At the other edge portion of the floor circling arm 74, an arm support 73 having an arm support rotation axis z2 parallel to the z-direction is rotatably mounted in the arrow direction c.

Further, on a side surface of the arm brace member 73, an arm holder 72 is rotatably mounted so as to rotate around an arm main rotation axis z3 parallel to the y-direction in the arrow b direction. On the side surface of the arm holder 72, the C arm 71 is mounted so as to freely slide in the direction of the arrow a around the arm slide center axis z4. Each edge of the C arm 71, an X-ray generating unit 2 and an X-ray detecting unit 3 are mounted so as to face each other.

The X-ray detecting unit 3 mounted at one edge portion of the C arm 71 can be moved in the arrow e direction. Further, the X-ray detecting unit 3 can be freely rotated around the imaging system rotation axis z5 in the arrow f direction in conjunction with the movable collimator 22 provided in the X-ray generating unit 2.

Each of the units constructing the holding unit 7 includes a C arm slide mechanism for sliding the C arm 71 in the a-direction around the arm slide center axis z4, a holder rotation mechanism for rotating the arm holder 72 in the b-direction around the arm main rotation axis z3, a support rotation mechanism for rotating the arm support 73 around the arm support rotation axis z2 in the c-direction and a floor circling arm rotation mechanism for rotating the floor circling arm 74 around the floor rotation axis z1 in the d-direction (all are not shown). Further, each of the units in the holding unit 7 includes an imaging system moving mechanism for moving the X-ray detecting unit 3 in the e-direction and an imaging system rotating mechanism for rotating the X-ray detecting unit 3 around the imaging system rotation axis z5 in the f-direction (both are not shown).

The bed unit 8 includes a vertical direction moving mechanism for moving up and down the top plate 81 for placing the object 150 in the h-direction (z-direction), and a horizontal direction moving mechanism for sliding the top plate 81 in a longitudinal direction ga (y-direction) or a traversing direction gb (x-direction) (both are not shown).

By rotating or moving both the holding unit 7 and each unit provided in the bed unit 8 in a prescribed direction, the imaging system provided at edge portions of the C arm 71 can locate at an appropriate position or a direction for X-ray imaging of an object 150 placed on the top plate 81. Thus, a desired imaging direction can be set up.

Figure 9:
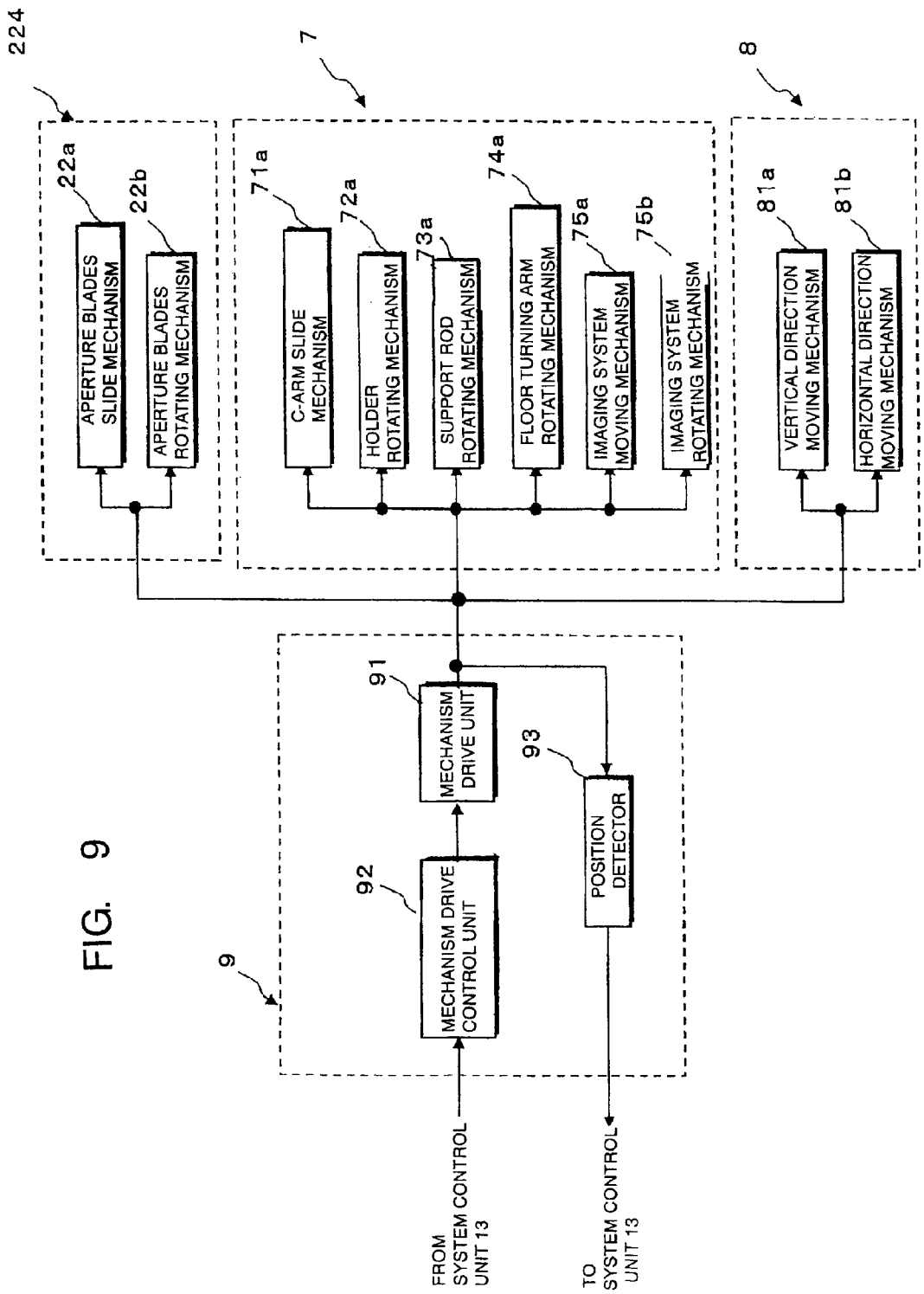
FIG. 9 is a block diagram illustrating various moving mechanisms provided in the movable collimator, the holding unit and the bed unit depicted in FIG. 1.

The moving mechanism drive unit 9 (FIG. 1) includes a mechanism drive unit 91, a mechanism drive control unit 92 and a position detecting unit 93. FIG. 9 illustrates a practical embodiment of the moving mechanism drive unit 9 for supplying drive signals to the movable collimator 22 in the X-ray generating unit 2 and various moving mechanisms provided in the holding unit 7 and the bed unit 8.

The aperture blade moving mechanism 224 provided in the movable collimator 22 includes an aperture blade sliding mechanism 22a and an aperture blade turning mechanism 22b. The aperture blade sliding mechanism 22a slides the aperture blade 221 in the A-direction so as to approach or secede to or from a center axis Cr of X-ray beams. The aperture blade turning mechanism 22b rotates the aperture blade 221 in the B-direction at a periphery of the center axis Cr.

The holding unit 7 includes a C-arm sliding mechanism 71a, a holder turning mechanism 72a, a support post rotating mechanism 73a, floor circling arm rotating mechanism 74a, an imaging system moving mechanism 75a and an imaging system rotating mechanism 75b. The C-arm sliding mechanism 71a is provided at a connecting portion of the C-arm 71 and the arm holder 72. The C-arm sliding mechanism 71a slides the C-arm 71 in the a-direction. The holder turning mechanism 72a is provided at a connecting portion of the arm holder 72 and the arm support post 73, and rotates the arm holder 72 in the b-direction. The support post rotating mechanism 73a is provided at a connecting portion of the arm support post 73 and the floor circling arm 74, and rotates the arm support post 73 in the c-direction. The floor circling arm rotating mechanism 74a is provided at a connection portion of the floor circling arm 74 and a floor surface 160, and rotates the floor circling arm 74 in the d-direction. Further, an imaging system moving mechanism 75a and an imaging system rotating mechanism 75b are provided at a connecting portion of the edge of the C-arm 71 and the X-ray detecting unit 3. The imaging system moving mechanism 75a moves the X-ray detecting unit 3 in the e-direction. The imaging system rotating mechanism 75b rotates the X-ray detecting unit 3 in the f-direction.

A vertically moving mechanism 81a and a horizontally moving mechanism 81b are provided in the bed unit 8. The vertically moving mechanism 81a lifts the top plate 81 for placing an object 150 up and down in the h-direction. The horizontally moving mechanism 81b slides the top plate 81 in the ga-direction and the gb-direction.

Drive signals generated by the mechanism drive unit 91 based on the control signals supplied from the mechanism drive control unit 92 in the moving mechanism drive unit 9 are supplied to the aperture blade sliding mechanism 22a and the aperture blade rotating mechanism 22b in the aperture blade moving mechanism 224, C-arm sliding mechanism 71a in the holding unit 7, the holder turning mechanism 72a, the support post rotating mechanism 73a, the floor circling arm rotating mechanism 74a, the imaging system moving mechanism 75a and the imaging system rotating mechanism 75b, and the vertically moving mechanism 81a and the horizontally moving mechanism 81b in the bed unit 8.

Thus, by controlling the above-described moving mechanisms based on the control signals generated in the mechanism drive control unit 92, as illustrated in FIG. 5B, aperture blades 221a-221d can be moved at appropriate positions so as that an opening formed by the aperture blades 221 almost coincide with a size of the examination target region. Further, the imaging system provided at the edges of the C-arm 71 can be placed at a desired position to an object 150 placed on the top plate 81.

The position detecting unit 93 in the moving mechanism drive unit 9 detects position data of the imaging system provided on the C-arm 71 and position data of the top plate 81 based on the drive signals generated by the mechanism drive unit 91. The position detecting unit 93 further calculates imaging directions to the object 150 by using these position data. The acquired imaging direction data is supplied to the projection data memory 61 in the image data generating unit 6 through the system control unit 13. The imaging direction data is stored together 2D projection data acquired in the imaging directions θa and θb during a preliminary imaging mode or 2D projection data acquired in the imaging directions θ1 trough θM during an actual imaging mode as collateral data for the projection data.

Figure 10:
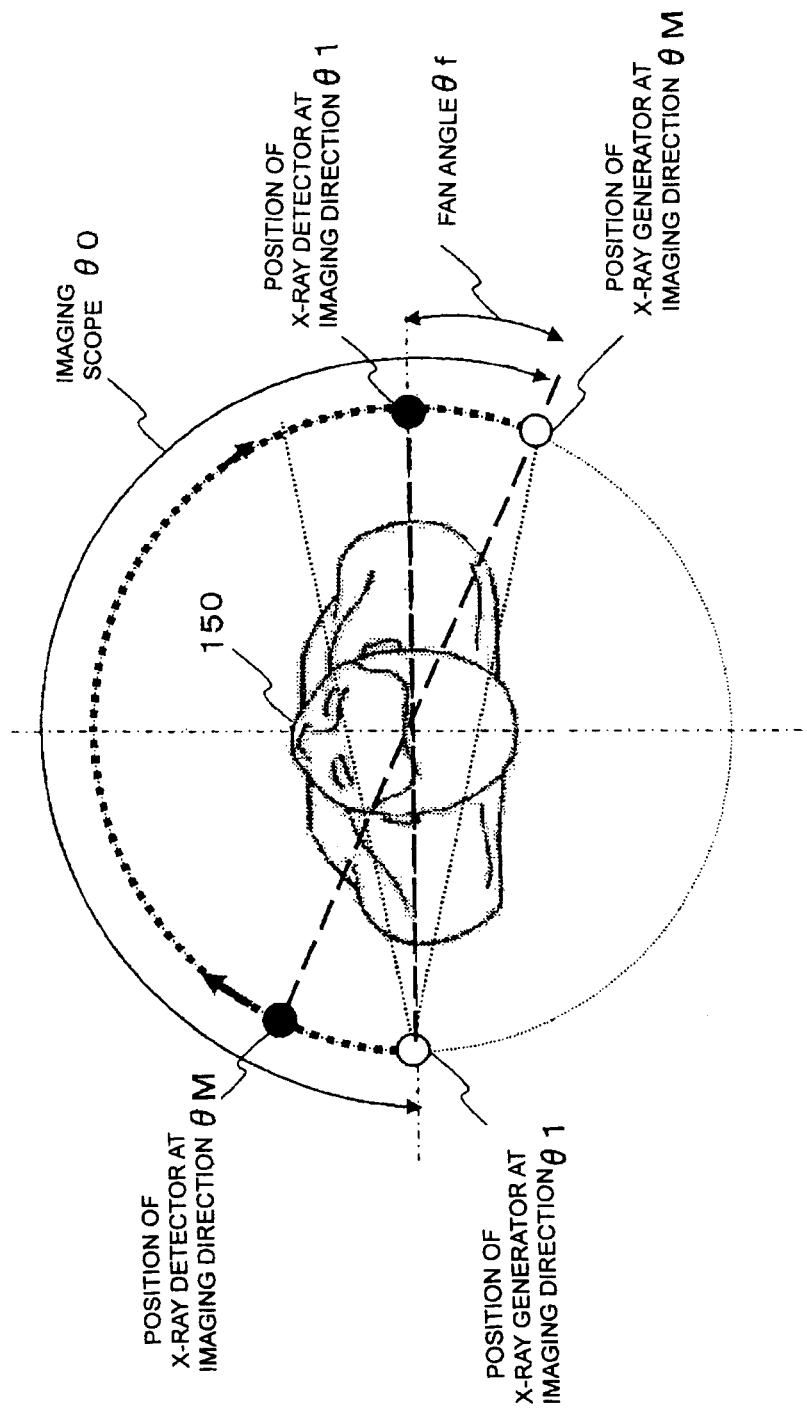
FIG. 10 shows imaging directions and imaging scopes in an actual imaging mode.

FIG. 10 illustrates the imaging directions and the imaging scopes during an actual imaging mode in the embodiment consistent with the present invention. The imaging system is continuously rotated around a periphery an object 150 both before administrating a contrast agent and after administrating the contrast agent. Then, X-ray imaging along the imaging directions θ1 through θM are performed by sliding and rotating the aperture blade 221a-221ds in the movable collimator 22 in a prescribed direction. Based on the acquired mask projection data and the contrast projection data, 3D image data is generated by reconstructing difference projection data in the imaging direction θ1 through θM. FIG. 10 depicts an imaging scope θ0 for acquiring the minimally required difference projection data for performing the reconstruction process. For the reconstruction process, it is needed to acquire a plurality of difference projection data at a prescribed angular interval in the scope of 180 degrees plus a fun angle θf.

In this case, the imaging system is rotated by the C-arm sliding mechanism 71a provided in the holding unit 7 or by the holder turning mechanism 72a (FIG. 9). The sliding and rotating movements of the aperture blades 221a through 221d are executed by the aperture blade sliding mechanism 22a and the aperture blade rotating mechanism 22b constructing the aperture blade moving mechanism 224 in the movable collimator 22. The fan angle θf shown in FIG. 10 is determined based on the X-ray irradiation angle emitted from the X-ray generating unit 2.

The display unit 10 (FIG. 1) includes a display data generator, a data converter and a monitor (all are not shown). The display data generator composes (provides in parallel) 2D image data in the imaging directions θa and θb supplied from the image processing unit 62 in the image data generating unit 6 in a preliminary imaging mode. Further, when an interest point is designated by the input unit 12 for indicating an edge portion of a device (stent) placed in a blood vessel in the examination target site, the display data generator generates a first display data by overlapping the 3D region of interest data set up on the examination target portion by the region of interest setting unit 11 based on the interest point data supplied from the input unit 12 and this interest point over the 2D image data. The display data generator further generates a second display data by adding collateral data, such as object data and X-ray imaging conditions to the 3D image data supplied from the rendering process unit 65 in the image data generating unit 6 in an actual imaging mode. The data converter converts the first and second display data into a prescribed displaying format. The converted display data is displayed on a monitor by performing D/A conversion and the television format conversion.

Figure 11:
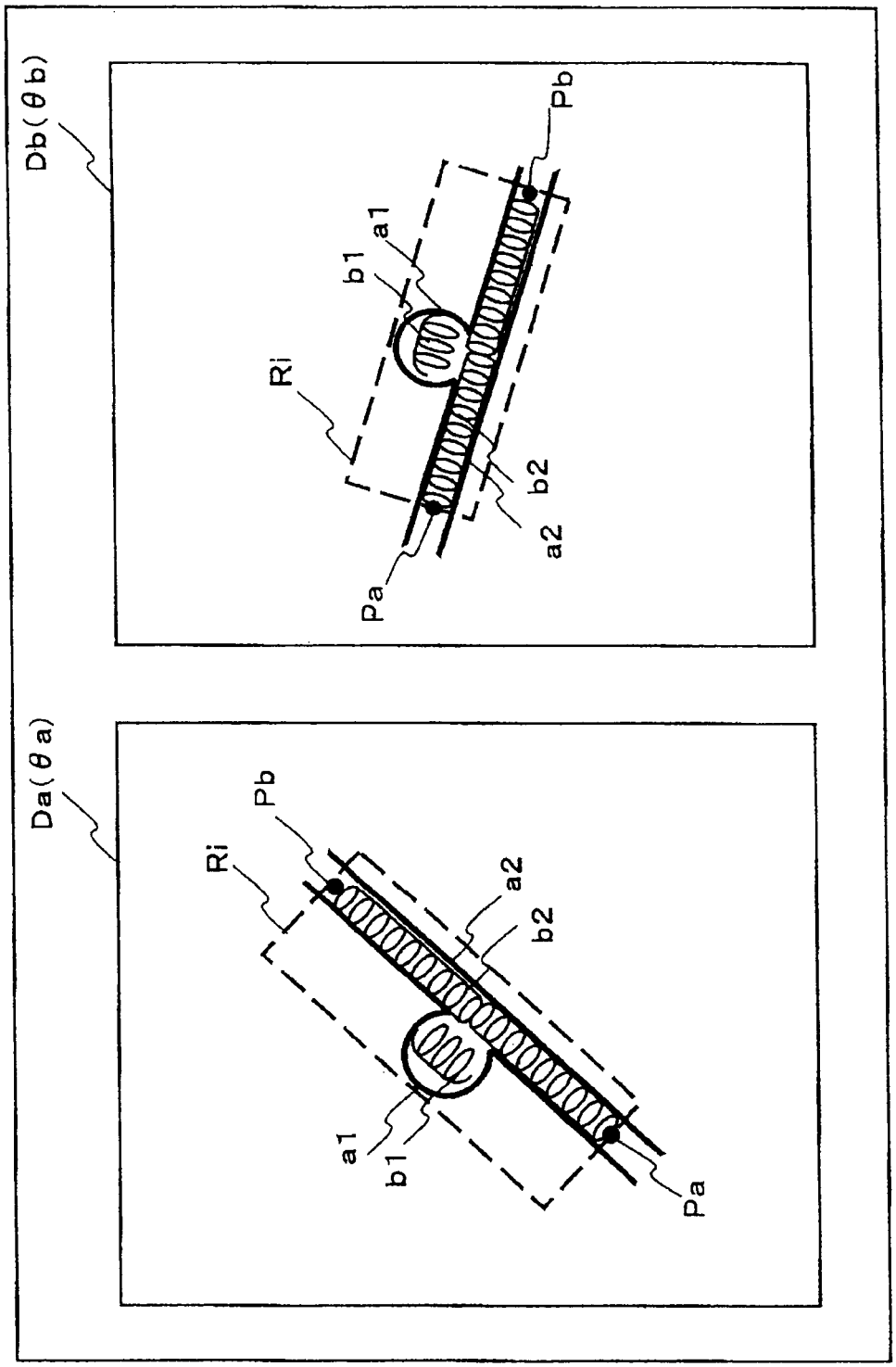
FIG. 11 illustrates an interest point designated in the examination target portion of 2D image data in a preliminary imaging mode and 3D region of interest set up based on the position data of the interest point.

FIG. 11 illustrates the first display data displayed on a monitor in the display unit 10 in the preliminary imaging mode, interest points designated by the input unit 12 on the examination target region of the first display data and 3D region of interest set up by the region of interest setting unit 11 based on the position data of the interest points.

As illustrated in FIG. 11, 2D image data Da (θa) and Db (θb) acquired along the imaging directions θa and θb in the preliminary imaging mode are displayed on the monitor in the display unit 10 as the first display data. Through the input unit 12, interest points Pa and Pb are designated at the edge portions of the stent b2 put in the blood vessel a2 displayed in the first display data at the examination target region. By receiving the position data of the interest point, the region of interest setting unit 11 (FIG. 1) sets up a 3D region of interest surrounding the examination target region Ri.

Thus, in the preliminary imaging mode, the first display data displayed on the monitor in the display unit 10 is constructed by arranging 2D image data Da (θa) acquired in the imaging direction θa and 2D image data Db (θb) acquired in the imaging direction θb orthogonally crossing the imaging direction θa in parallel. As shown in FIG. 11, in each of 2D image data Da (θa) and Db (θb), a coil b1 placed in aneurysm a1 and a stent b2 put in the blood vessel a2 are displayed as the examination target region. When such a first display data is displayed in the display unit 10, an operator designates the interest points Pa and Pb for indicating edges of the stent b2 in each of 2D image data Da (θa) and Db (θb) by using an input device, such as a mouse, provided in the input unit 12. The position data of interest points Pa and Pb are supplied to the system control unit 13 through the input unit 12. By receiving the position data, the region of interest setting unit 11 sets up a 3D region of interest Ri of a length determined based on a line segment connecting the interest points Pa and Pb and a width determined outside edges of the blood vessel a2 and the aneurysm a1.

By designating the interest points Pa and Pb in each of 2D image data Da (θa) and Db (θb), it becomes possible to identify the position coordinate of the edge portions of the stent in a 3D space. Accordingly, the region of interest setting unit 11 can sets up a 3D region of interest in the examination region based on the interest points Pa and Pb.

The input unit 12 (FIG. 1) includes an imaging mode selection unit 121 for selecting an imaging mode, an imaging condition setting unit 122 for setting up X-ray imaging conditions including X-ray irradiation conditions and an interest point designating unit 123 for designating an interest point to the 2D image data in the preliminary imaging mode. The input unit 12 inputs object data and various command signals through input devices, such as a display panel, a keyboard, a mouse, etc. The input unit 12 further sets up lengths and widths of 3D region of interest, and designates imaging directions both in the preliminary imaging mode and the actual imaging mode and image data generating conditions.

The system control unit 13 includes a CPU and a memory circuit (both not shown). The system control unit 13 stores the input data and the set up data supplied from the input unit 12 into the memory circuit. Then, based on these data, the system control unit 13 totally controls each unit in the X-ray diagnosis apparatus to generate and display 2D image data in the preliminary imaging mode and 3D image data in the actual imaging mode.

Figure 12:
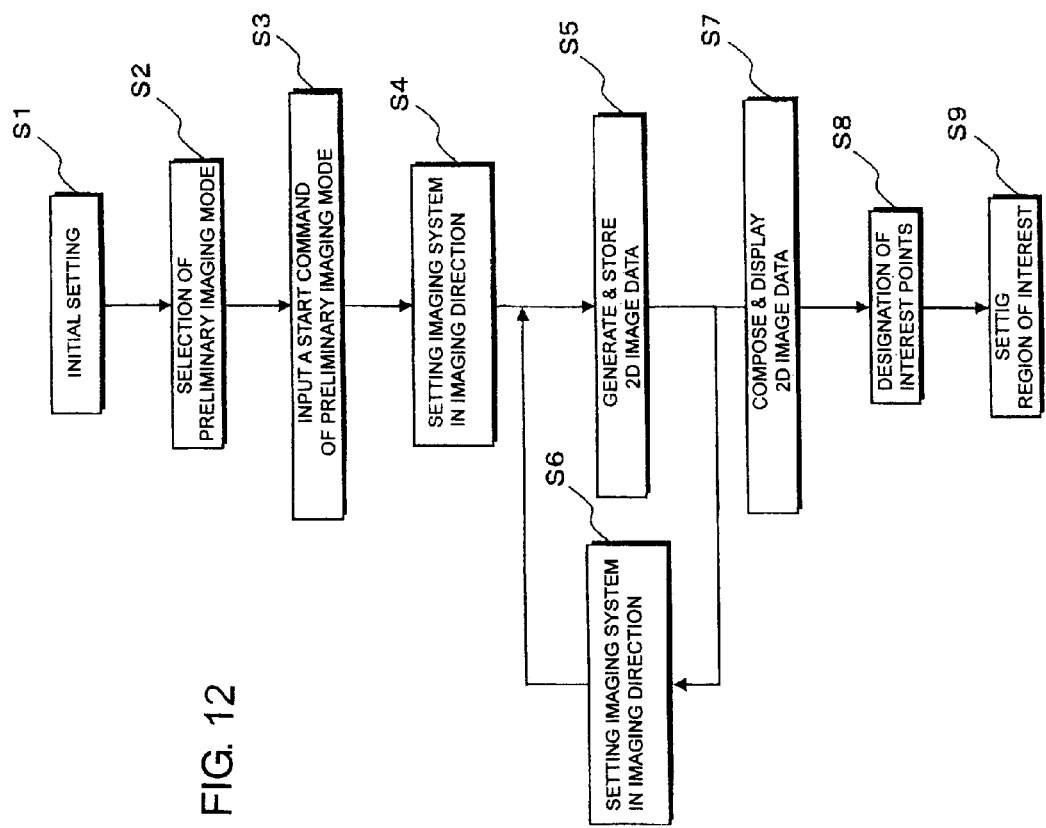
FIG. 12 is a flowchart for setting up the 3D region of interest in the preliminary imaging mode.

FIG. 12 is a flowchart illustrating a setting up process of 3D region of interest in the preliminary imaging mode according to the present embodiment.

Prior to perform X-ray imaging to an object 150 in the preliminary imaging mode, an operator of an X-ray diagnosis apparatus 100 performs an initial set up the apparatus through the input unit 12 (FIG. 12, step S1). Thus, after inputting the object data, X-ray imaging conditions including X-ray irradiation conditions, the imaging directions θa and θb in the preliminary imaging mode, imaging directions θ1 through θM in the actual imaging mode, image data generating conditions and lengths and widths of 3D region of interest are set up. These input and set up data are stored in the memory circuit of the system control unit 13.

When the apparatus has been initially set up, the operator selects the preliminary imaging mode through the input unit 12 (FIG. 12, step S2) after moving the top plate 81 placing an object 150 to a prescribed position, and inputs a start command for the preliminary imaging mode (FIG. 12, step S3). By supplying this command signal to the system control unit 13, an X-ray imaging in the preliminary imaging mode is started.

Thus, by receiving the start command signal of the preliminary imaging mode, the system control unit 13 reads out the set up data of the imaging directions θa and θb from the self memory circuit, and supplies them to the mechanism drive control unit 92 in the moving mechanism unit 9. By receiving the set up data, the mechanism drive control unit 92 supplies a mechanism drive control signal generated based on the set up data in the imaging direction θa to the mechanism drive unit 91. The mechanism drive unit 91 generates a drive signal based on the mechanism drive control signal, and supplies to the holder turning mechanism 72a in the holding unit 7 to set up the imaging system in the imaging direction θa by rotating the C arm 71 (FIG. 12, step S4).

Then, the system control unit 13 supplies X-ray irradiation conditions read out from the memory circuit and the X-ray generating command signal to the X-ray control unit 51 in the high voltage generating unit 5. The X-ray control unit 51 controls the high voltage generator 52 based on the X-ray irradiation conditions to supply a high voltage to the X-ray tube 21 in the X-ray generating unit 2. The X-ray tube 21 irradiates X-rays for the preliminary imaging mode onto the object 150 in a prescribed period through the movable collimator 22. The X-rays penetrated through the object 150 are detected by the plane detector 31 in the X-ray detecting unit 3.

In the plane detector 31, each photoelectric film 312 arranged in each detection elements 311 accumulates a signal charge proportioned to the X-rays penetrated through the object 150 to the capacitor 313. When the X-ray irradiation has finished, the gate driver 32 receives clock pulses from the system control unit 13 and successively reads out the accumulated signal charge from the capacitor 313 $y$ supplying drive pulses to TFT 314 in the plane detector 31.

The read out signal charge is converted into a voltage in the charge/voltage converter 41 of the projection data generating unit 4. Further, the A/D converter 42 converts the voltage to digital signal and stores in the buffer memory in the parallel/serial converter 43 as projection data of a one line. The parallel/serial converter 43 reads out the projection data from the buffer memory in serial by a line, and successively stores into the projection data memory 61 in the image data generating unit 6 to generate 2D projection data.

The image processing unit 62 generates 2D image data along the imaging direction θa by performing imaging processes to 2D projection data generated in the projection data memory 61. The generated 2D image data is stored in the memory circuit of the image processing unit 62 (FIG. 12, step S5).

When the storing of 2D image data along the imaging direction θa has finished, the system control unit 13 controls the moving mechanism drive unit 9 to set up the imaging system in the imaging direction θb substantially orthogonal to the imaging direction θa (FIG. 12, step S6). Further, the system control unit 13 controls to generate and store 2D image data along the imaging direction θb as described the step S5.

When 2D image data in the imaging directions θa and θb have been generated and stored, the display unit 10 displays the 2D image data along the imaging directions θa and θb read out from the memory circuit in the image processing unit 62 by arranging in parallel on the monitor (FIG. 12, step S7). By observing the two 2D image data displayed on the monitor, the operator designates the interest point at each edge portion of the stent put in the blood vessel displayed in the examination target region of 2D image data input unit 12 by using an input device (FIG. 12, step S8).

The position data of the interest point is supplied to the region of interest setting unit 11 through the system control unit 13. The region of interest setting unit 11 sets up a 3D region of interest surrounding the examination target region based on the position data (FIG. 12, step S9).

Figure 13:
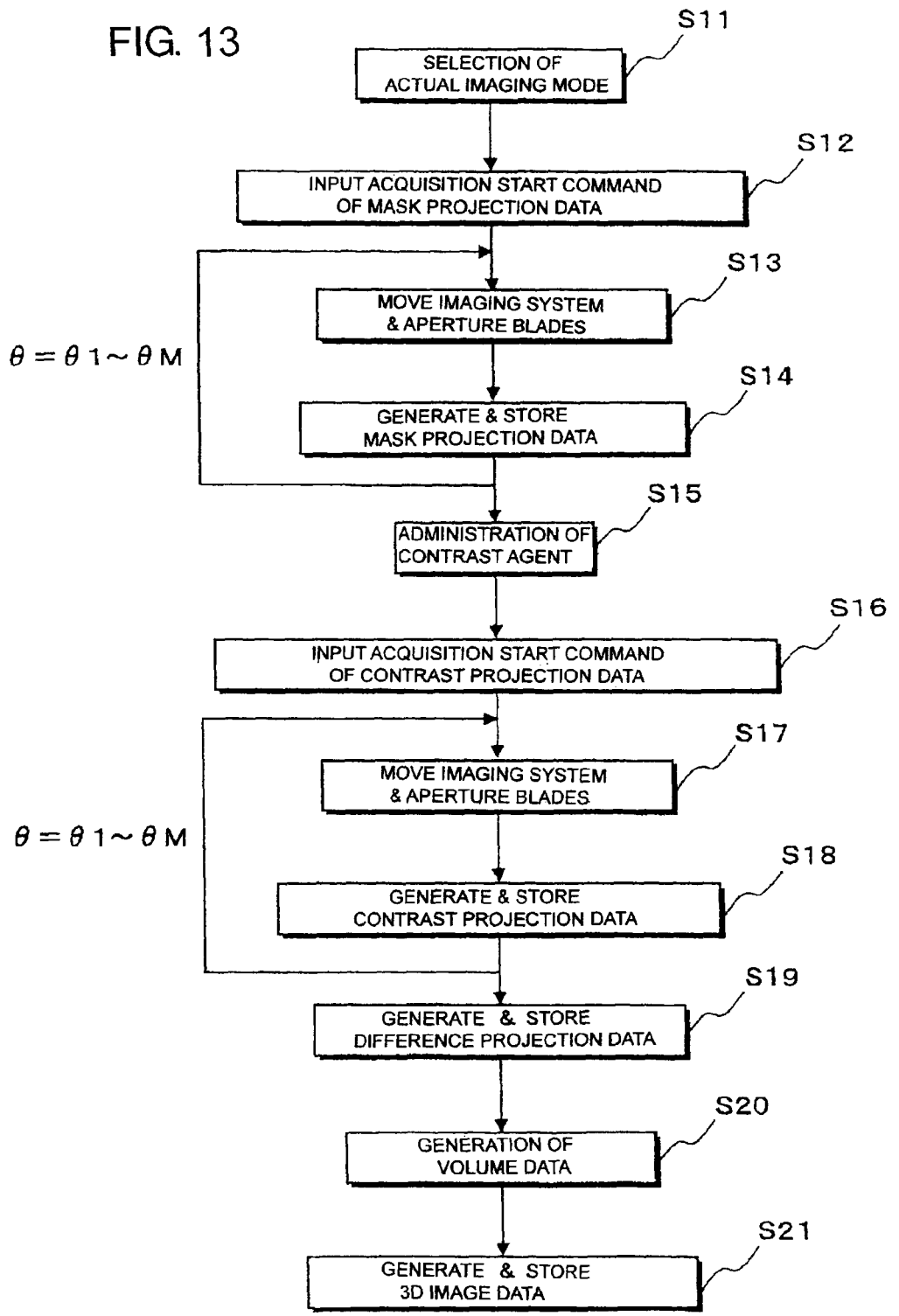
FIG. 13 is a flowchart for generating and displaying the 3D image data in an actual imaging mode.

FIG. 13 is a flowchart illustrating generating and displaying steps of 3D image data in an actual imaging mode consistent with the present embodiment.

When the setting of a 3D region of interest to the examination target region has finished at the step S9 in FIG. 12, the operator selects an actual imaging mode through the input unit 12 (FIG. 13, step S11). Further, a start command for acquiring mask projection data is input by using the input unit 12 (FIG. 13, step S12). By supplying the acquisition start command signal to the system control unit 13, an acquisition of the mask projection data of the object 150 in the actual imaging mode is started.

Thus, by receiving the acquisition start command signal, the system control unit 13 reads out the set up data on the imaging directions θ1 through θM in the actual imaging mode from the self memory circuit and supplies them to the mechanism drive control unit 92 in the moving mechanism drive unit 9. By receiving these set up data, the mechanism drive control unit 92 mechanism initially supplies a mechanism drive control signal generated based on the set up data along the imaging direction θ1 to the mechanism drive unit 91. The mechanism drive unit 91 supplies a drive signal generated based on the mechanism drive control signal and supplies to the holder turning mechanism 72a in the holding unit 7 for setting up the imaging system supported on an edge portion of the C-arm 71 in the first imaging direction θ1.

Further, the system control unit 13 supplies a 3D region of interest data set up in the region of interest setting unit 11 to the mechanism drive control unit 92 in the moving mechanism drive unit 9. By receiving the set up data, the mechanism drive control unit 92 supplies a mechanism drive control signal generated based on a projected figure of the 3D region of interest in the first imaging direction θ1 to the mechanism drive unit 91. The mechanism drive unit 91 generates a drive signal based on the mechanism drive control signal and supplies it to the aperture blade moving mechanism 224 in the movable collimator 22 so as to locate the aperture blades 221a-221d by sliding and turning at an appropriate position for an X ray irradiation to the examination target region (FIG. 13, step S13).

Then, the system control unit 13 supplies X-ray irradiation conditions read out from the memory circuit and the X-ray generating command signal to the X-ray control unit 51 in the high voltage generating unit 5. Based on the X-ray irradiation conditions, the high voltage control unit 41 supplies a high voltage to the X-ray tube 21 by controlling the X-ray generating unit 2. The X-ray tube 21 irradiates X-rays to the object 150 through the movable collimator 22 in a prescribed period. The X-rays penetrated through the object 150 are detected by the X-ray detecting unit 3.

The projection data generating unit 4 generates projection data by performing processes of the detected signals in the X-ray detecting unit 3. By successively storing the acquired projection data in the projection data memory 61, mask projection data in the imaging direction θ1 is generated (FIG. 13, step S14).

When the acquisition of mask projection data along the imaging direction θ1 has finished, the system control unit 13 successively rotates the imaging system in each of the imaging directions θ2 through θM by controlling each unit. Further, by sliding and rotating the aperture blades 221a-221d in the movable collimator 22 based on the projected figure of 3D region of interest in these imaging directions, X-ray imaging is performed onto the object 150. The projection data supplied in time series from the X-ray imaging unit 1 is successively stored in the projection data memory 61 for generating mask projection data along each of the imaging directions θ2 through θM. Thus, by repeating the steps S13 and S14, the mask projection data generated along each of the imaging directions θ1 through θM is stored in the projection data memory 61 together the imaging direction as collateral data.

Then, the operator administrates a contrast agent into the object 150 (FIG. 13, step S15). At a time when the contrast agent reaches to the examination target region, a contrast projection data acquisition start command is input through the input unit 12 (FIG. 13, step S16). By receiving the contrast projection data acquisition start command, the system control unit 13 moves the imaging system and the aperture blades by totally controlling each of units in the X-ray diagnosis apparatus 100 (FIG. 13, step S17). Further, the system control unit 13 performs X-ray imaging in the actual imaging mode along the imaging direction θ1 through θM for generating and storing the contrast projection data (FIG. 13, step S18).

Acquisition of the mask projection data and the contrast projection data along the imaging direction θ1 through θM have finished, the subtraction process unit 63 reads out the mask projection data before administrating the contrast agent and the contrast projection data after administrating the contrast agent acquired in these imaging directions together the collateral data, i.e., the imaging direction data from the memory circuit in the projection data memory 61, and generates a plurality M of difference projection data corresponding to the imaging directions θ1 through θM by performing a subtraction process between the mask projection data and the contrast projection data that are acquired along the same imaging direction. The difference projection data is stored in the memory circuit in the reconstruction processing unit 64 by adding the direction data of the imaging directions θ1 through θM (FIG. 13, step S19).

The reconstruction processing unit 64 reads out and performs reconstruction processes of the difference projection data based on the collateral data of the imaging directions θ1 through θM to generate volume data (FIG. 13, step S20). Then, the rendering process unit 65 sets up an opacity degree and a color tone based on voxel value of the volume data generated by the reconstruction processing unit 64. By performing a rendering process of the volume data based on the set up opacity degree and the color tone and a viewing point and a visual line direction supplied from the input unit 12, the rendering process unit 65 generates 3D image data (FIG. 13, step S21).

According to the above-mentioned rendering process, for generating image data based on projection data acquired through X-ray irradiations to a region of interest of an object, unnecessary X-ray irradiations to the periphery of the region of interest can be inhibited by sliding and rotating the aperture blades in the collimator based on a figure of the region of interest having a strong directionality. As a result, exposure dose to the object during the X-ray imaging can be reduced.

Particularly, since the sliding amount and the rotation angle are optimized by each of imaging directions, appropriate and sufficient projection data for a reconstruction process can be acquired, image data of good quality can be generated through an X-ray imaging of a low exposure dose.

According to the embodiment consistent with the present invention, the aperture blades provided in the movable collimator are constructed so as that a shielding amount becomes gradually smaller into a center portion. Accordingly, even when an X-ray irradiation is performed to a relatively narrow region through the aperture blades, the intensity distribution near the periphery of projection data does not significantly change. Consequently, high quality image data can be generated by reducing artifacts due to non-continuity of projection data.

Since the above-described aperture blades are constructed by a plurality of X-ray shielding plates that can independently slide to the center direction of the X-ray beam, it becomes possible to form the intensity distribution of the projection data in accordance with the examination target region so as to restrain occurrence of artifacts.

The embodiments of the present invention can be modified. For instance, while the stent is put in the normal blood vessel running a periphery of the aneurysm for preventing the coil slipping off from the neck portion of the aneurysm in the embodiments, it is possible to put a stent in the blood vessel to prevent a resteonis of a blood vessel that is treated by a balloon catheter. Further, it is possible to perform the X-ray imaging to a blood vessel in which a device does not put in. The examination target region having a strong directionality may include lumen other than a blood vessel.

In the exemplary embodiments, a plurality of interest points is designated to 2D image data acquired along two orthogonal imaging directions. Then, 3D region of interest surrounding an examination target region is set up based on these interest points. Of course, in the preliminary imaging mode, it needs not to use such two orthogonal imaging directions. For instance, 3D region of interest can be set up based on 2D image data acquired along more than three imaging directions.

While the interest points are designated to a plurality of 2D image data acquired by the usual X-ray imaging in the above-described embodiments, it is also possible to designate the interest point on 3D image data acquired by using the digital subtraction angiography (DSA) method or the usual X-ray imaging. Further, the designation of the interest points is not limited to the edge portion of the medical treatment devices put in a blood vessel displayed on the image data, but can voluntarily be designate to the blood vessel or the devices put in the blood vessel.

In the above-described exemplary embodiments, a running direction of a blood vessel is detected based on the interest points and 3D region of interest having a prescribed length and a width is set up along the running direction. It is also possible to designate the length and the width region of interest can be set based on an outline data of the blood vessel and the devices put in the blood vessel by automatically extracting from the image data in a preliminary imaging mode. Further, X-ray imaging in an actual imaging mode can be performed based on the 3D region of interest data of the examination target portion preliminarily measured by the X-ray diagnosis apparatus or another image diagnosis apparatus.

In the exemplary embodiments, the setting of an imaging direction is performed by rotating the imaging system. It is also possible to perform by sliding the C arm having the imaging system.

In the above-described exemplary embodiments, the plurality of aperture blades are turned so that an effective X-ray irradiation is performed on an examination target portion having a particular directionality. It is also possible to rotate the collimator itself by stead of rotating the aperture blades.

While certain embodiments, the X-ray imaging in an actual imaging mode generates the volume data based on the difference projection data generated by using the DSA and 3D image data is generated based on the volume data, the volume data can be generated based on 2D projection data acquired through a normal X-ray imaging. The image data generated based on the volume data does not limit to 3D image data. For instance, the image data generated based on the volume data may includes multi-planar reconstruction (MPR) image data generated at a prescribed slice plane of the volume data and maximum intensity projection (MIP) image data projected the volume data in a prescribed direction.

While certain embodiments have been described, these embodiments are presented by way of example only, and are not intended to limit the scope of the invention. Indeed, the novel methods and systems described herein may be embodied in a variety of other forms; furthermore, various omissions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An X-ray diagnosis apparatus comprising:
   an X-ray tube configured to generate X-rays to an examination target having a particular directionality;
   an X-ray detecting unit configured to detect X-rays penetrated through the examination target;
   an X-ray collimating unit including a plurality of aperture blades provided between the X-ray tube and the X-ray detecting unit for setting an effective X-ray irradiation region on the examination target by sliding and turning the plurality of aperture blades so that an effective X-ray irradiation is performed on the examination target depending upon the particular directionality;

a driving unit configured to rotationally move the X-ray tube and the X-ray detecting unit;

a region of interest setting unit configured to set up a region of interest on the examination target by executing a preliminary imaging mode for performing two 2D image reconstruction processes on the examination target along two imaging directions substantially orthogonal with each other, and designating region points on each of the two 2D reconstructed images;

an X-ray aperture controlling unit configured to control the X-ray collimating unit so as to slide and turn the plurality of aperture blades in correspondence with the rotational movements, based on set up data of the region of interest and the two imaging directions, and an image data generating unit configured to generate image data for performing a 3D image reconstruction process based on each of position data of the region points designated on the two 2D reconstructed images and projection data acquired in correspondence with the rotational movements of the X-ray tube and the X-ray detecting unit.

2. The X-ray diagnosis apparatus according to claim 1, wherein the X-ray aperture controlling unit slides each of the aperture blades in an approaching direction or a seceding direction to or from the center axis of X-ray beams based on the set up data of the region of interest, and turns them all about the center axis of the X-ray beams.

3. The X-ray diagnosis apparatus according to claim 1, wherein the driving unit and the X-ray aperture controlling unit set up X-ray imaging directions by rotating or moving the imaging system including the X-ray tube, the X-ray collimating unit and the X-ray detecting unit around the periphery of the examination target, and slide and rotate the aperture blades based on a projected figure of the 3D region of interest in the two imaging directions.

4. The X-ray diagnosis apparatus according to claim 1, wherein each of the aperture blades is constructed so that an X-ray shielding amount is gradually reduced toward a tip portion of the blade.

5. The X-ray diagnosis apparatus according to claim 4, wherein each of the aperture blades is constructed by piling up a plurality of X-ray shielding plates, each plate can independently slide in an approaching or a seceding direction to or from the center axis of X-ray beams; and the X-ray aperture controlling unit controls a moving amount of the X-ray shielding plate in accordance with the examination target.

6. The X-ray diagnosis apparatus according to claim 4, wherein each of the aperture blades is constructed by piling up a plurality of X-ray shielding plates, each plate can independently slide in an approaching or a seceding direction to or from the center axis of X-ray beams; and the X-ray aperture controlling unit controls an inclination of the X-ray shielding plate in accordance with the thickness of the examination target.

7. The X-ray diagnosis apparatus according to claim 1, wherein the image data generating unit generates difference projection data by performing a subtraction process between the projection data before administrating a contrast agent and contrast projection data after administrating the contrast agent, and generates at least one of 3D image data, MIP (maximum intensity projection) image data and MPR (multi-planar reconstruction) image data by performing a reconstruction process of the difference projection data acquired along each of the imaging directions.

8. The X-ray diagnosis apparatus according to claim 1, wherein each of the aperture blades is constructed so that the thickness of blade is gradually increased with going toward an outer edge portion of the blade.

9. A method for controlling an X-ray irradiation region comprising:

generating X-rays from an X-ray tube to an examination target having a particular directionality;

detecting X-rays penetrated through the examination target by an X-ray detecting unit;

setting up an effective X-ray irradiation region on the examination target by sliding and turning a plurality of aperture blades so that an effective X-ray irradiation is performed on the examination target depending upon the particular directionality through an X-ray collimating unit;

rotationally moving the X-ray tube and the X-ray detecting unit;

setting up a region of interest to the examination target by executing a preliminary imaging mode for performing two 2D image reconstruction processes on the examination target along two imaging directions substantially orthogonal with each other, and designating region points on each of the two 2D reconstructed images;

controlling the X-ray collimating unit so as to slide and move the plurality of aperture blades in correspondence with the rotational movement based on set up data of the region of interest and the two imaging directions, and to control movement of each aperture blade in the planar direction; and generating image data for performing a 3D image reconstruction process based on each of position data of the region points designated on the two 2D reconstructed images and projection data acquired in correspondence with the rotational movements of the X-ray tube and the X-ray detecting unit.

* * * * *